US012796968B2

(12) United States Patent
Kim et al.

(10) Patent No.: US 12,796,968 B2
(45) Date of Patent: Nov. 17, 2026

(54) MECHANOCHROMIC ARRAY PATCH AND METHOD FOR MANUFACTURING THE SAME

(71) Applicant: Electronics and Telecommunications Research Institute, Daejeon (KR)

(72) Inventors: Jae Joon Kim, Daejeon (KR); Chan Woo Park, Daejeon (KR); Seong Hyun Kim, Daejeon (KR); Sujung Kim, Daejeon (KR); Bock Soon Na, Daejeon (KR); Jeho Na, Daejeon (KR); Su Jae Lee, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 419 days.

(21) Appl. No.: 18/486,850

(22) Filed: Oct. 13, 2023

(65) Prior Publication Data

US 2024/0130638 A1 Apr. 25, 2024
US 2024/0225484 A9 Jul. 11, 2024

(30) Foreign Application Priority Data

Oct. 21, 2022 (KR) ........................ 10-2022-0136803

(51) Int. Cl.
*A61B 5/11* (2006.01)
*A61B 5/00* (2006.01)
(Continued)

(52) U.S. Cl.
CPC .......... *A61B 5/1126* (2013.01); *A61B 5/6833* (2013.01); *A61B 5/7445* (2013.01);
(Continued)

(58) Field of Classification Search
CPC ... A61B 5/1126; A61B 5/6833; A61B 5/7445; A61B 2562/0266; A61B 2562/046;
(Continued)

(56) References Cited

U.S. PATENT DOCUMENTS

2007/0132722 A1 6/2007 Kim et al.
2010/0137749 A1 6/2010 Jeong et al.
(Continued)

FOREIGN PATENT DOCUMENTS

JP 4267658 5/2009
KR 10-1940551 1/2019
(Continued)

OTHER PUBLICATIONS

Guo et al., "A review of mechanochromic polymers and composites: From material design strategy to advanced electronics application", Composites Part B, Oct. 22, 2021, pp. 1-18, vol. 227.
(Continued)

*Primary Examiner* — Justin Xu
(74) *Attorney, Agent, or Firm* — KILE PARK REED & HOUTTEMAN PLLC

(57) ABSTRACT

Disclosed is a mechanochromic array patch that implements, as a color change, a strain applied to a skin surface due to musculoskeletal movement. The mechanochromic array patch may include stretchable mechanochromic color-changing parts, a polymer connection part that connects the mechanochromic color-changing parts, and a water-insoluble support part. The polymer connection part may have a higher elastic modulus compared to the mechanochromic color-changing parts.

9 Claims, 11 Drawing Sheets

(51) Int. Cl.
*A61L 15/30* (2006.01)
*A61L 15/56* (2006.01)

(52) U.S. Cl.
CPC ............... *A61L 15/30* (2013.01); *A61L 15/56* (2013.01); *A61L 2420/02* (2013.01)

(58) Field of Classification Search
CPC ... A61B 5/45; A61B 5/11; A61L 15/30; A61L 15/56; A61L 2420/02; G01D 7/005
See application file for complete search history.

(56) References Cited

U.S. PATENT DOCUMENTS

| | | | | |
|---|---|---|---|---|
| 2016/0250373 | A1* | 9/2016 | Munro | A61F 13/0206 602/48 |
| 2023/0381089 | A1* | 11/2023 | Chrysanthakopoulos | A61K 8/0208 |
| 2023/0382153 | A1* | 11/2023 | Antonakis | B43K 8/00 |

FOREIGN PATENT DOCUMENTS

| | | |
|---|---|---|
| KR | 10-2022-0077216 | 6/2022 |
| KR | 10-2022-0077497 | 6/2022 |
| KR | 10-2022-0102784 | 7/2022 |

OTHER PUBLICATIONS

Park et al., "A Hierarchical Nanoparticle-in-Micropore Architecture for Enhanced Mechanosensitivity and Stretchability in Mechanochromic Electronic Skins", Advanced Materials, May 9, 2019, pp. 1-10, vol. 31.

Sandilands et al., "Capturing Close Interactions with Objects Using a Magnetic Motion Capture System and a RGBD Sensor", Motion in Games, 2012, pp. 220-231.

Rozé et al., "Assessing the Effects of a Primary Control Impairment on the Cellists' Bowing Gesture Inducing Harsh Sounds", IEEE Access, Aug. 28, 2018, pp. 43683-43695, vol. 6.

Hordyj, "Inverse Kinematics of anthropomorphic structures for vision systems applications", AGH University, Oct. 2015, pp. 1-73.

Lin et al., "A Modular Data Glove System for Finger and Hand Motion Capture Based on Inertial Sensors", Journal of Medical and Biological Engineering, 2019, pp. 532-540. vol. 39.

Qingyun et al., "Research advance on key technology of EMG-based Control for Hand Exoskeleton Robots", 4 total pages.

Kim et al., "A deep-learned skin sensor decoding the epicentral human motions", Nature Communications, May 1, 2020, pp. 1-8, vol. 11.

* cited by examiner

MECHANOCHROMIC ARRAY PATCH AND METHOD FOR MANUFACTURING THE SAME

CROSS-REFERENCE TO RELATED APPLICATIONS

This U.S. non-provisional patent application claims priority under 35 U.S.C. § 119 of Korean Patent Application No. 10-2022-0136803, filed on Oct. 21, 2022, the entire contents of which are hereby incorporated by reference.

BACKGROUND

The present disclosure herein relates to a mechanochromic array patch, and more particularly, to a mechanochromic array patch that implements, as a color change, a mechanical strain applied to a skin surface due to musculoskeletal movement.

A wearable element technology that implements a functional element and a system thereof on a human body is widely applied in various forms for musculoskeletal system movement analysis and disease diagnosis due to the advantages of high convenience and easy reflection of actual body movement. Such wearable elements provide information about the state and movement of a musculoskeletal system through direct biometric signal measurement or indirect methods via an additional system connected to the outside. The state of a musculoskeletal system may be detected and a disease may be diagnosed by analyzing the information, and the measurement is performed in a particular environment or everyday life according to the type of wearable equipment.

However, according to typical methods, information can be obtained only at a particular point in time not continuously since an element has physical properties different from those of human skin, and the degree of integration of the element is limited. Furthermore, such typical methods have a limitation in that instead of a strain of each site of skin under a patch, a strain of a film itself may be reflected, and are restrictively applied only to unidirectional large movement of a joint rather than complex movement of a musculoskeletal system over a wide area in order to avoid this limitation.

SUMMARY

The present disclosure provides a mechanochromic array patch including mechanochromic color-changing parts arranged in an array form.

The present disclosure also provides a method for manufacturing a mechanochromic array patch including mechanochromic color-changing parts arranged in an array form.

An embodiment of the inventive concept provides a mechanochromic array patch including: stretchable mechanochromic color-changing parts, which are arranged in a two-dimensional array form; a polymer connection part that connects the mechanochromic color-changing parts adjacent to each other; and a water-insoluble support part. In an embodiment, the polymer connection part may have a higher elastic modulus compared to the mechanochromic color-changing parts. In an embodiment, each of the mechanochromic color-changing parts may be configured to change in color according to a strain rate.

In an embodiment of the inventive concept, a method for manufacturing a mechanochromic includes: forming a sacrificial layer on a substrate; forming a polymer connection part of a linear type on the sacrificial layer; forming mechanochromic color-changing parts on both ends of the polymer connection part; forming a water-insoluble support part on the polymer connection part and the mechanochromic color-changing parts; and removing the sacrificial layer, wherein the polymer connection part has a higher elastic modulus compared to the mechanochromic color-changing parts.

BRIEF DESCRIPTION OF THE FIGURES

The accompanying drawings are included to provide a further understanding of the inventive concept, and are incorporated in and constitute a part of this specification. The drawings illustrate embodiments of the inventive concept and, together with the description, serve to explain principles of the inventive concept. In the drawings:

FIG. 2A is a plan view illustrating a mechanochromic array patch according to an embodiment;

FIG. 2B is a cross-sectional view of a mechanochromic array patch in an external force condition in which tensile stress is applied according to an embodiment;

DETAILED DESCRIPTION

Hereinafter, embodiments of the inventive concept will be described with reference to the accompanying drawings so that the configuration and effects of the inventive concept are sufficiently understood. However, the inventive concept is not limited to the embodiments described below, but may be implemented in various forms and may allow various modifications. Rather, these embodiments are provided so that this disclosure will be thorough and complete, and will fully convey the scope of the inventive concept to those skilled in the art.

The terminology used herein is not for delimiting the embodiments of the inventive concept but for describing the embodiments. The terms of a singular form may include plural forms unless otherwise specified. The term "include", "including", "comprise" and/or "comprising" used herein does not preclude the presence or addition of one or more other elements.

Hereinafter, a mechanochromic array patch and a manufacturing method thereof according to an embodiment of the inventive concept will be described with reference to the drawings.

Figure 1:
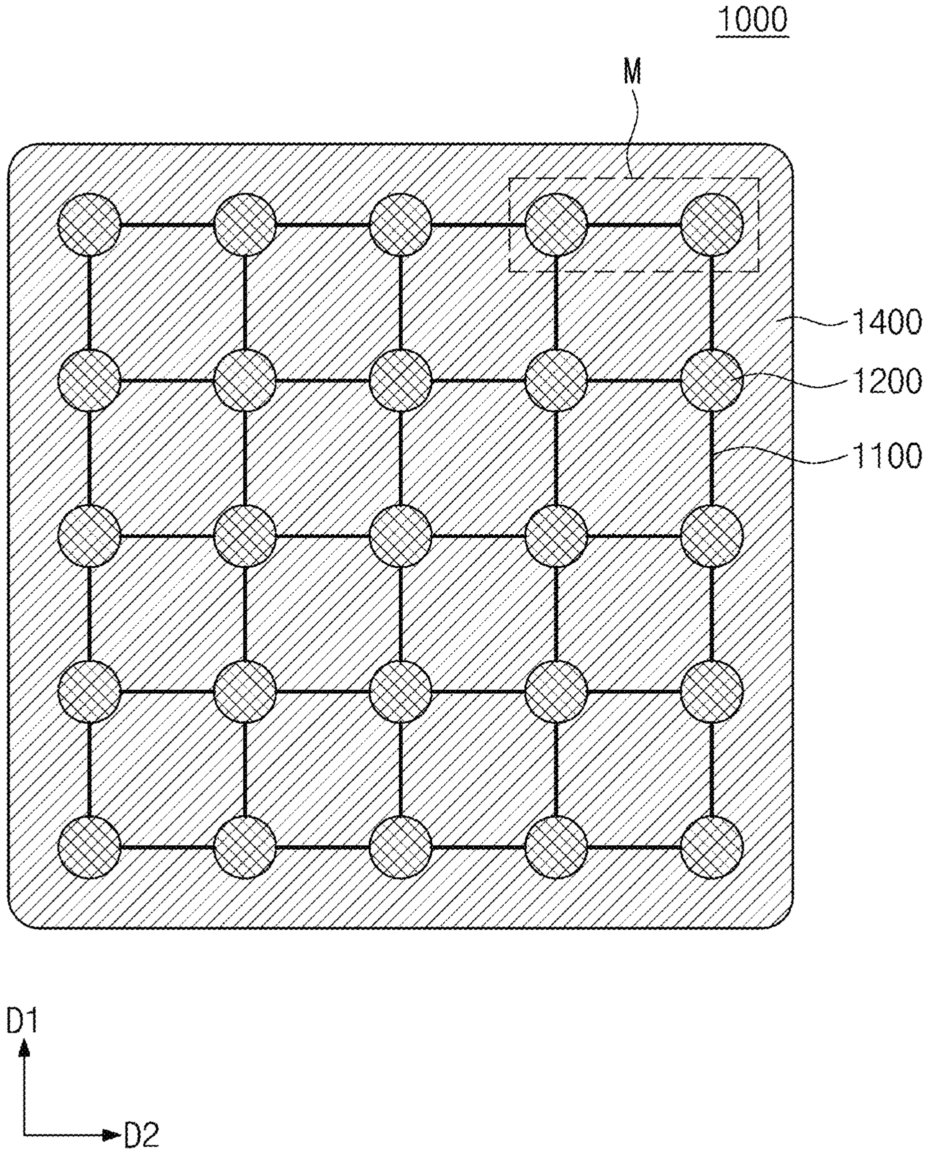
FIG. 1 is a plan view illustrating a mechanochromic array patch according to an embodiment.

FIG. 1 is a plan view for describing a mechanochromic array patch according to an embodiment.

Referring to FIG. 1, a mechanochromic array patch 1000 may include stretchable mechanochromic color-changing parts 1200, which are arranged two dimensionally, a polymer connection part 1100 that connects adjacent mechanochromic color-changing parts 1200, and a water-insoluble support part 1400. The polymer connection part 1100 may have a higher elastic modulus compared to the mechanochromic color-changing parts 1200.

The mechanochromic color-changing parts 1200 each may change in color according to a strain rate. For example, a color of a mechanochromic color-changing part to which tensile stress is applied may be different from a color of the mechanochromic color-changing part exhibited before the tensile stress was applied. The color-changing parts 1200 constituting the mechanochromic array patch may exhibit different colors according to a concentrated strain.

The mechanochromic color-changing parts 1200 each may include a stretchable polymer and mechanochromic material. The stretchable polymer may be formed of a material having a property that enables free change in a shape, such as stretchability. For example, the stretchable polymer may include polydimethylsiloxane, (PDMS), polybutylene adipate terephthalate (PBAT), and poly(styrene-block-butadiene styrene) (SBS). The mechanochromic material may include photonic crystal, piezophotonic materials, mechanophores-linked polymers, and microcrack structure.

In an embodiment of the inventive concept, the stretchable polymer may have an elastic modulus of about 0.5 MPa to about 80 MPa.

The mechanochromic color-changing parts 1200 may further include skin-adhesive material layer for attachment to skin. The material layer may include polyvinyl alcohol (PVA) and hydrogel.

Referring to FIG. 1, the mechanochromic color-changing parts 1200 adjacent to each other may be connected by the polymer connection part 1100 having a linear form. The polymer connection part 1100 may include a non-stretchable polymer. For example, the polymer connection part 1100 may include polyimide (PI), photoresist, and resin.

In an embodiment of the inventive concept, the non-stretchable polymer may have an elastic modulus of about 2 Gpa or more.

Referring to FIG. 1, the water-insoluble support part 1400 may be formed on the polymer connection part 1100 and the mechanochromic color-changing parts 1200. The water-insoluble support part 1400 may include water-insoluble materials such as polydimethylsiloxane (PDMS), polystyrene (PS), and poly(ethylene terephthalate) (PET).

Figure 2A:
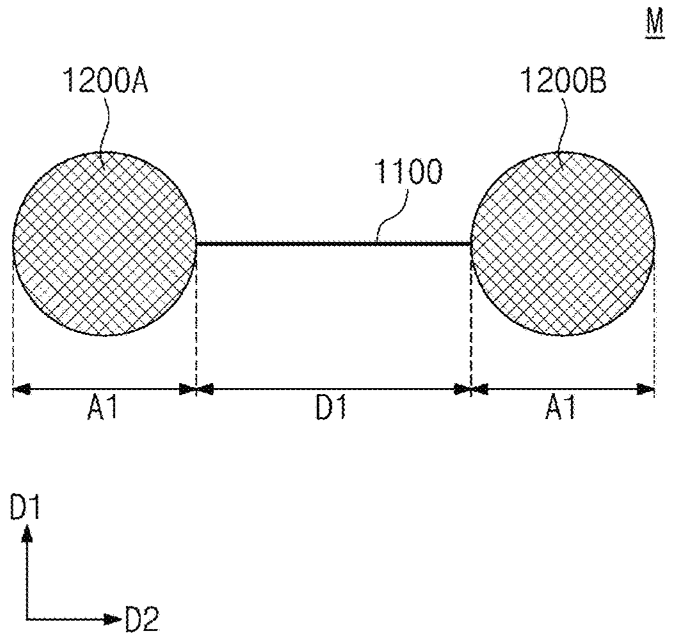
FIGS. 2A and 2B are enlarged plan views of the region M in the mechanochromic array patch of FIG. 1.
Figure 2B:
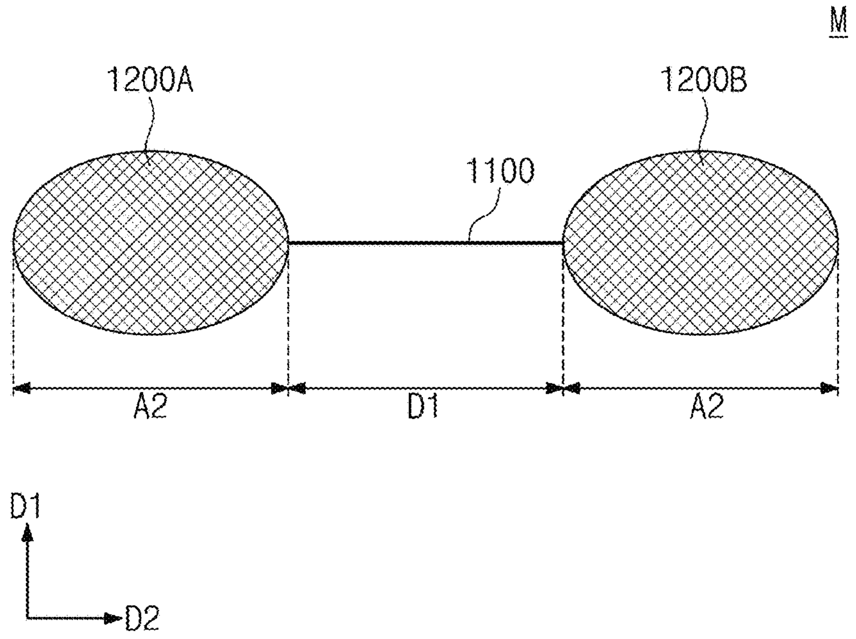

FIGS. 2A and 2B are enlarged plan views illustrating the region M of FIG. 1.

FIG. 2A illustrates a mechanochromic array patch before tensile stress is applied. Referring to FIG. 2A, mechanochromic color-changing parts 1200A and 1200B each may have a first width A1. The first mechanochromic color-changing part 1200A may be connected to the second mechanochromic color-changing part 1200B by the polymer connection part 1100 having a first length D1.

Referring to FIG. 2B, the mechanochromic array patch 1000 may be provided to an external force condition in which tensile force is applied. In the external force condition, the first and second mechanochromic color-changing parts 1200A and 1200B each may have a second width A2. The second width A2 may be larger than the first width A1. In the external force condition, the mechanochromic color-changing parts 1200A and 1200B may change in color according to a strain rate, and thus may exhibit different colors from those of the mechanochromic color-changing parts 1200A and 1200B of FIG. 2A. The strain rate of each of the mechanochromic color-changing parts 1200A and 1200B may be a difference between the second width A2 and the first width A1.

Referring to FIGS. 2A and 2B, since the polymer connection part 1100 may include a non-stretchable polymer, the length D1 of the polymer connection part of FIG. 2B may be substantially the same as the length D1 of the polymer connection part of FIG. 2A. Furthermore, even in the external force condition in which tensile stress is applied, the polymer connection part 1100 may have a small color change or no color change compared to the mechanochromic color-changing part 1200.

Referring back to FIG. 2A, when tensile stress applied to the mechanochromic array patch reduces, the mechanochromic color-changing parts 1200A and 1200B each may have the first width A1 again. Accordingly, the mechanochromic color-changing parts 1200A and 1200B may again exhibit colors exhibited before tensile stress was applied.

FIGS. 3A to 3D are diagrams illustrating a manufacturing process of a mechanochromic array patch. The same descriptions as provided above are omitted below.

Referring to FIG. 3, a manufacturing method of a mechanochromic array patch according to an embodiment of the inventive concept may include: forming a sacrificial layer on a substrate; forming a polymer connection part of a linear type on the sacrificial layer; forming mechanochromic color-changing parts on both ends of the polymer connection part; and removing the sacrificial layer.

The manufacturing method of a mechanochromic array patch according to an embodiment of the inventive concept includes forming a sacrificial layer 1300 on a substrate. The sacrificial layer 1300 may include polyethylene oxide (PEO), polyvinyl alcohol (PVA), polyacrylamide (PAAM), and/or polyacrylic acid (PAA).

Figure 3A:
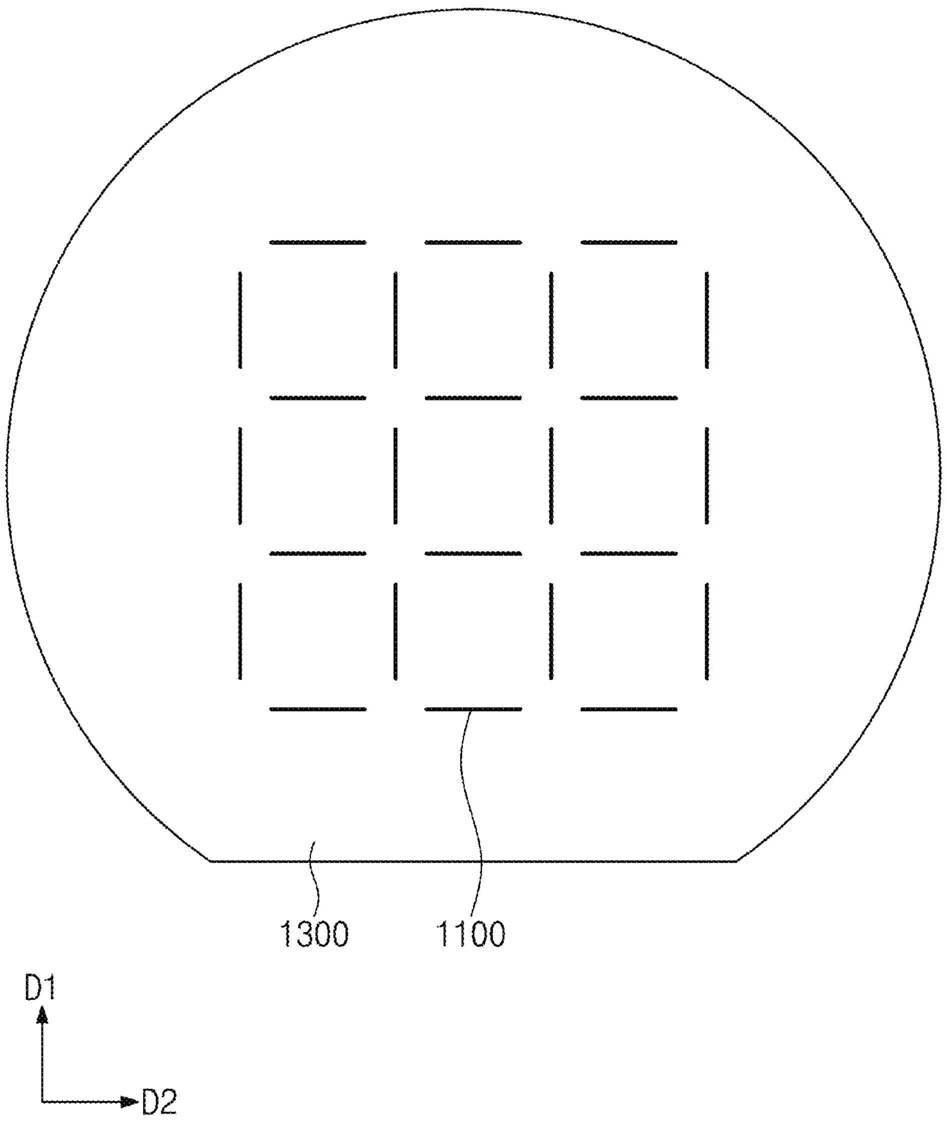
FIGS. 3A to 3D are diagrams illustrating a manufacturing process of a mechanochromic array patch according to an embodiment.
Figure 3B:
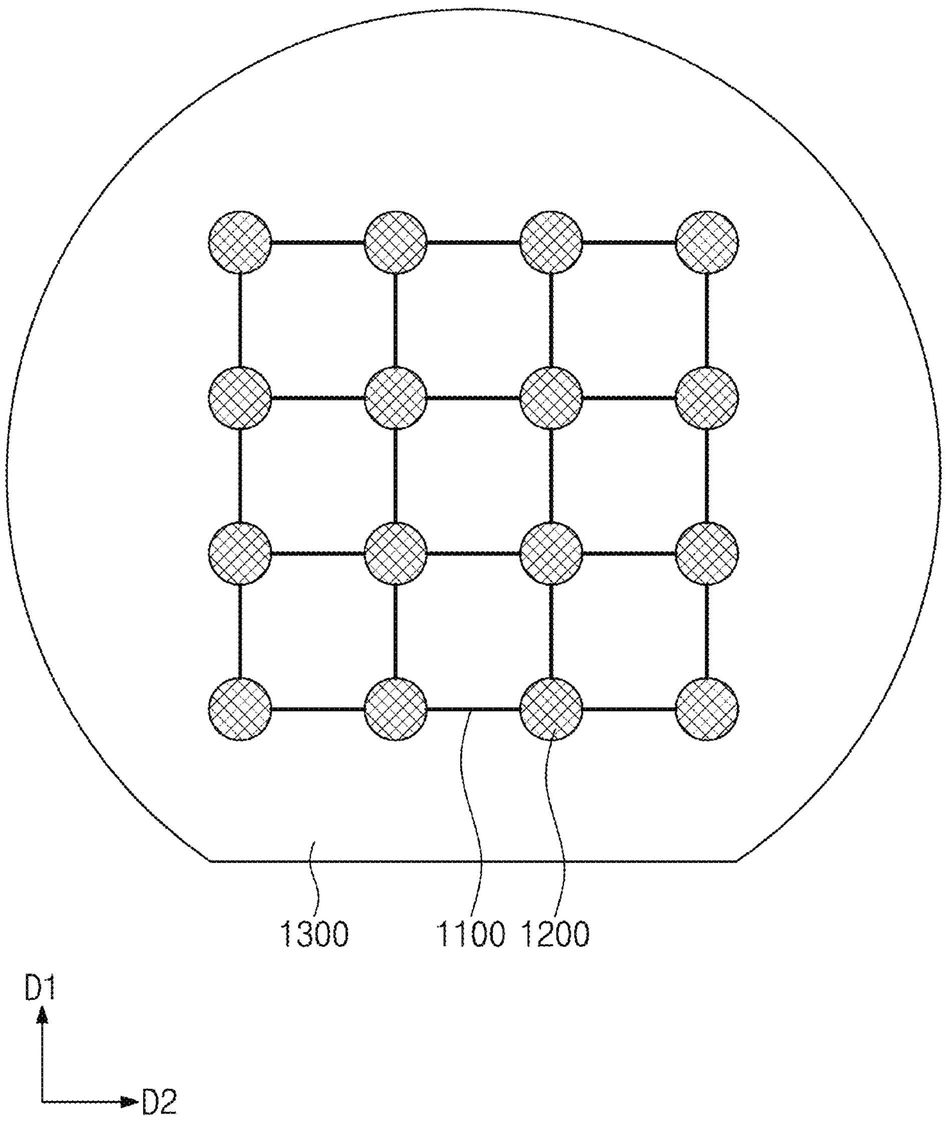
Figure 3C:
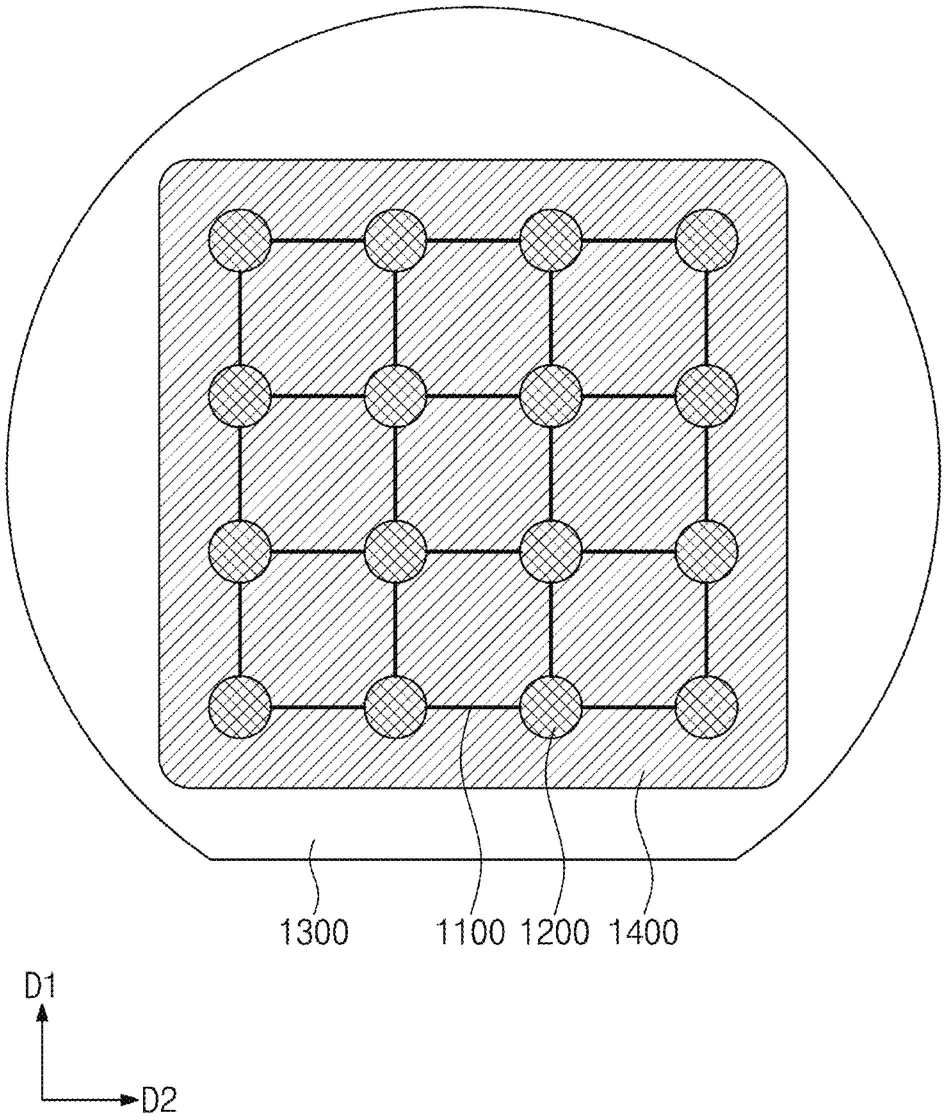

Referring to FIG. 3A, the polymer connection part 1100 of a linear type may be formed on the sacrificial layer 1300. Referring to FIG. 3B, the mechanochromic color-changing parts 1200 may be formed on both ends of the polymer connection part 1100. Referring to FIG. 3C, the water-insoluble support part 1400 may be formed on the polymer connection part 1100 and the mechanochromic color-changing parts 1200. Here, the water-insoluble support part 1400 may be formed by transferring a film onto the polymer connection part 1100 and the mechanochromic color-changing parts 1200.

Figure 3D:
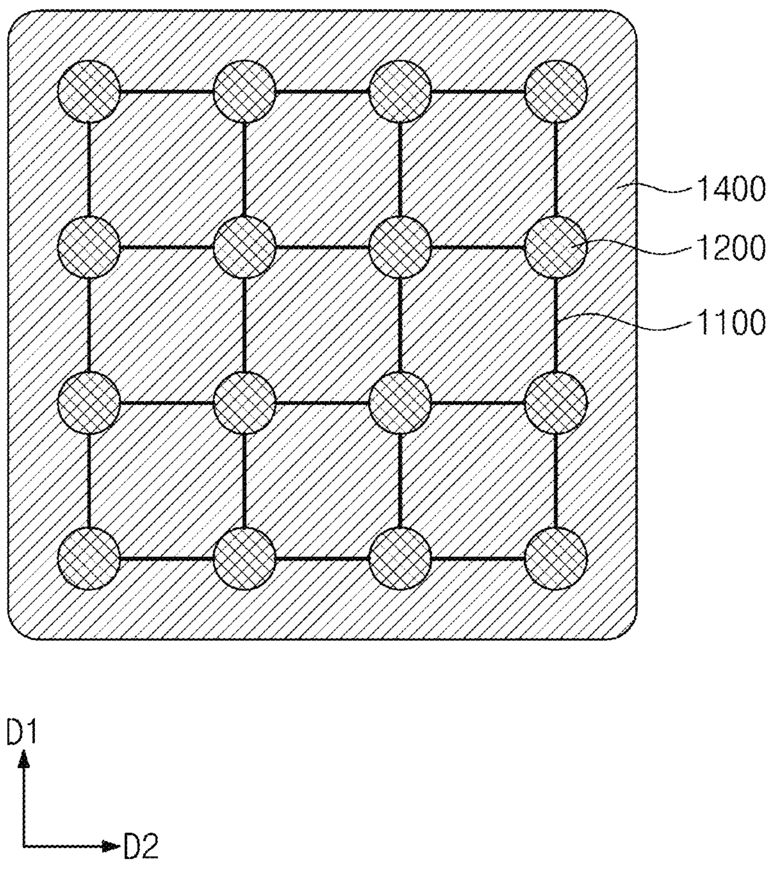

The manufacturing method of a mechanochromic array patch according to an embodiment of the inventive concept may include removing the sacrificial layer 1300 after forming of the water-insoluble support part 1400. FIG. 3D is a diagram illustrating the mechanochromic array patch transferred onto skin after the sacrificial layer 1300 is removed.

Figure 3E:
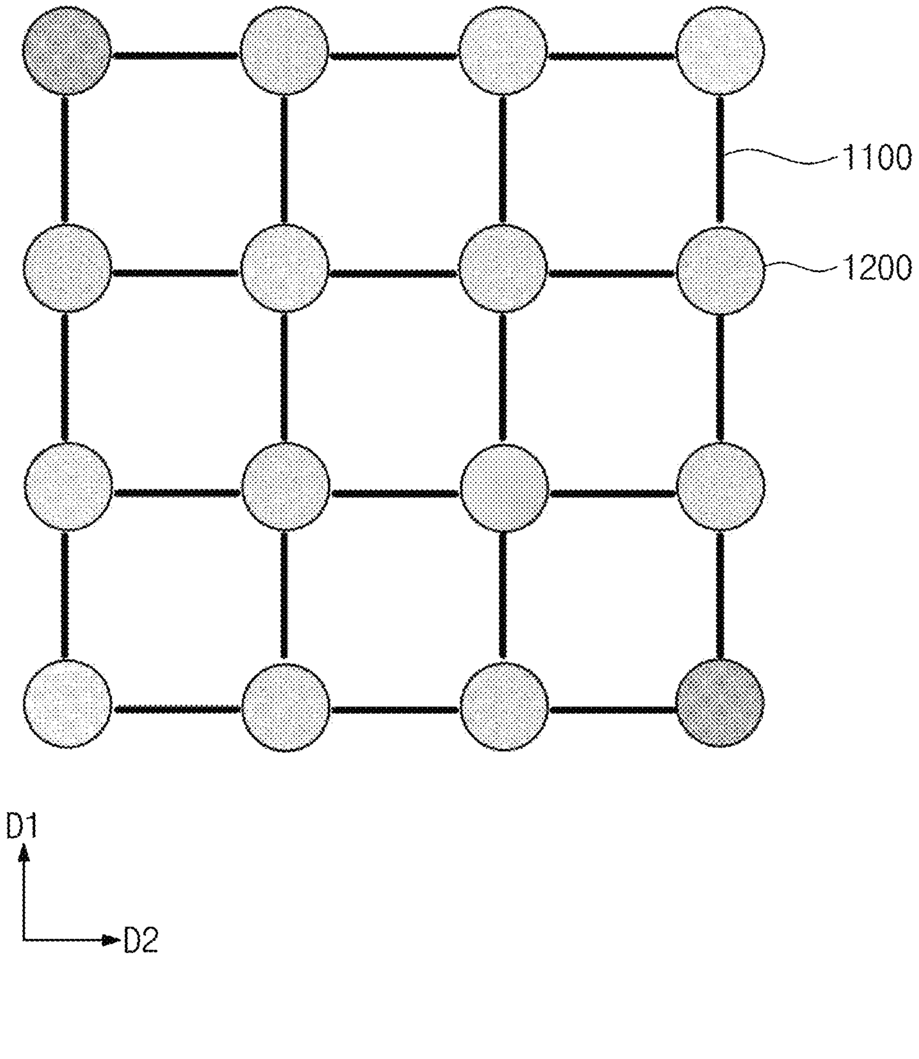
FIG. 3E is a diagram illustrating a shape of a mechanochromic array patch transferred onto skin according to an embodiment.

FIG. 3E is a schematic diagram illustrating a form in which the mechanochromic array patch according to an embodiment of the inventive concept has been transferred onto skin. Referring to FIG. 3E, after transferring the mechanochromic array patch of FIG. 3D, the support part 1400 for transferring to skin may be removed. The mechanochromic array patch attached onto skin may have a distribution of different strains internally according to movement of a musculoskeletal system under skin. The strain distribution may be exhibited as a color change of each of the mechanochromic color-changing parts 1200.

The polymer connection part 1100 has a higher elastic modulus compared to the mechanochromic color-changing parts 1200, and thus may less change or may not change in terms of length and thickness compared to the mechanochromic color-changing parts 1200. A color change of the mechanochromic color-changing parts 1200 may be used in analysis of strain locally concentrated on the mechanochromic color-changing parts 1200. Musculoskeletal movement under skin may be inferred through the strain analysis.

Figure 4:
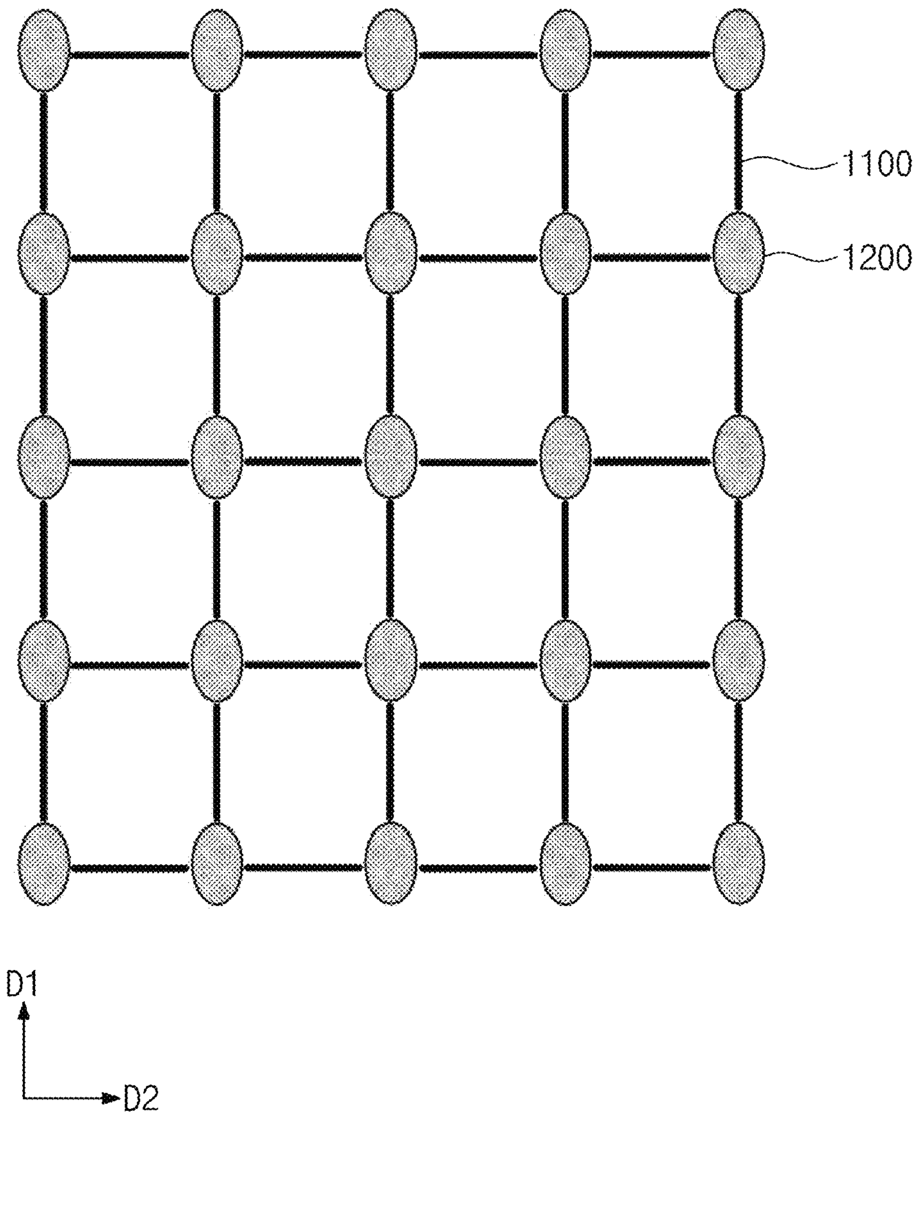
FIG. 4 is a diagram illustrating a mechanochromic array patch to which compression is applied according to an embodiment.
Figure 5:
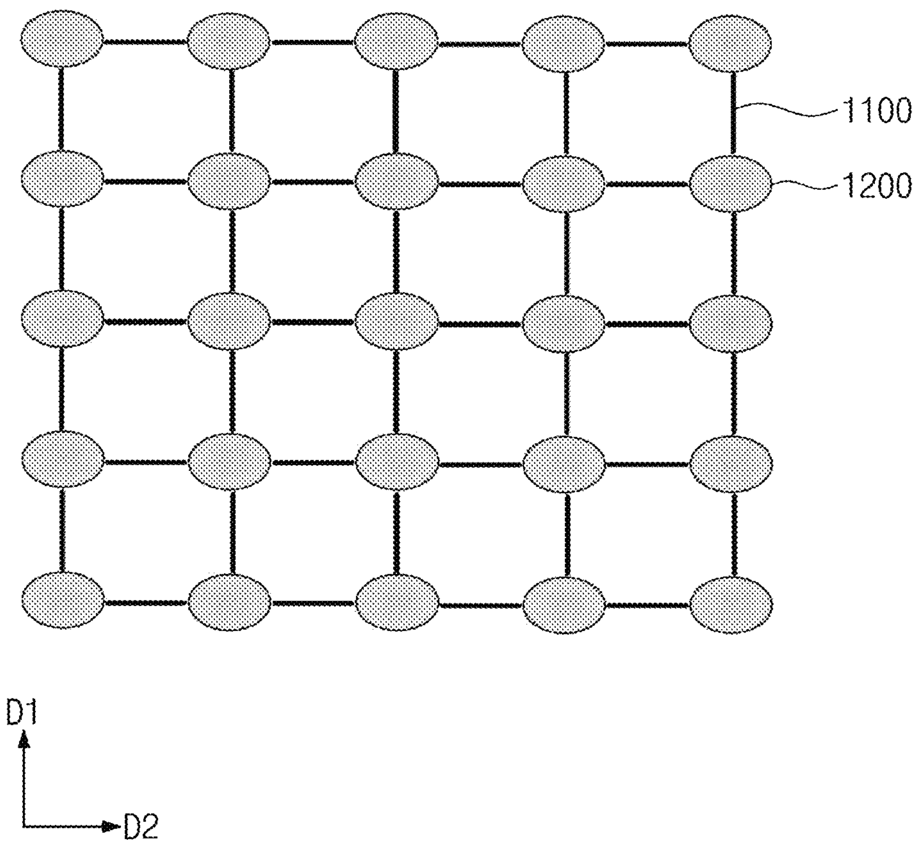
FIG. 5 is a diagram illustrating a mechanochromic array patch to which tensile stress is applied according to an embodiment.

FIGS. 4 and 5 are plan views illustrating a color change of a mechanochromic array patch according to an embodiment of the inventive concept. FIG. 4 is a diagram illustrating a skin-attached mechanochromic array patch to which compression is laterally applied when skin contracts. FIG. 5 is a diagram illustrating a mechanochromic array patch to which tensile stress is laterally applied when skin relaxes. In FIGS. 4 and 5, there may be a small change or no change in the length and thickness of the polymer connection part 1100 compared to the mechanochromic color-changing parts 1200.

Figure 6:
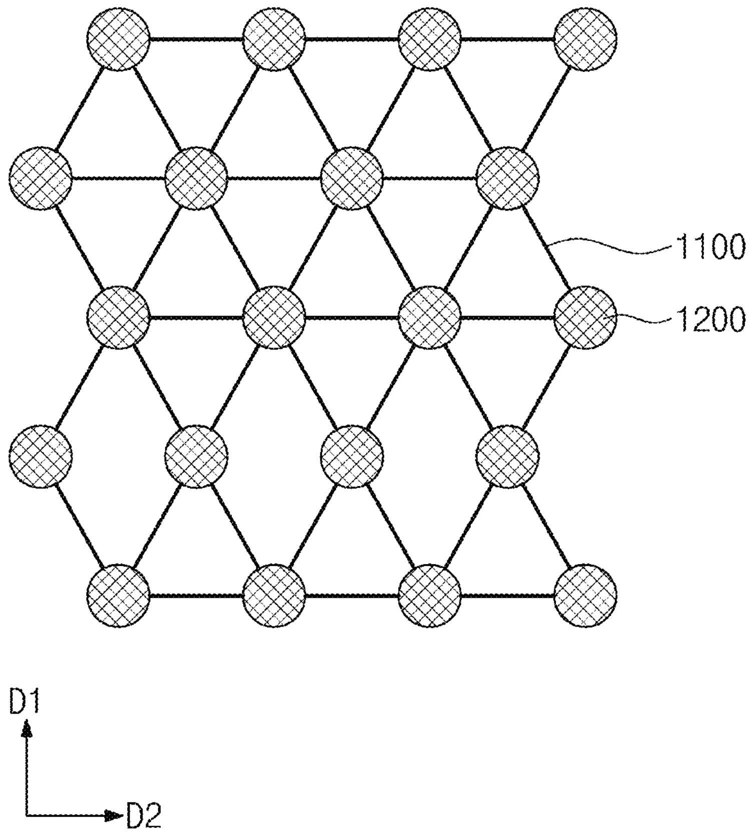
FIG. 6 is a plan view illustrating a mechanochromic array patch including a polymer connection part continuously connected in a triangular form.
Figure 7:
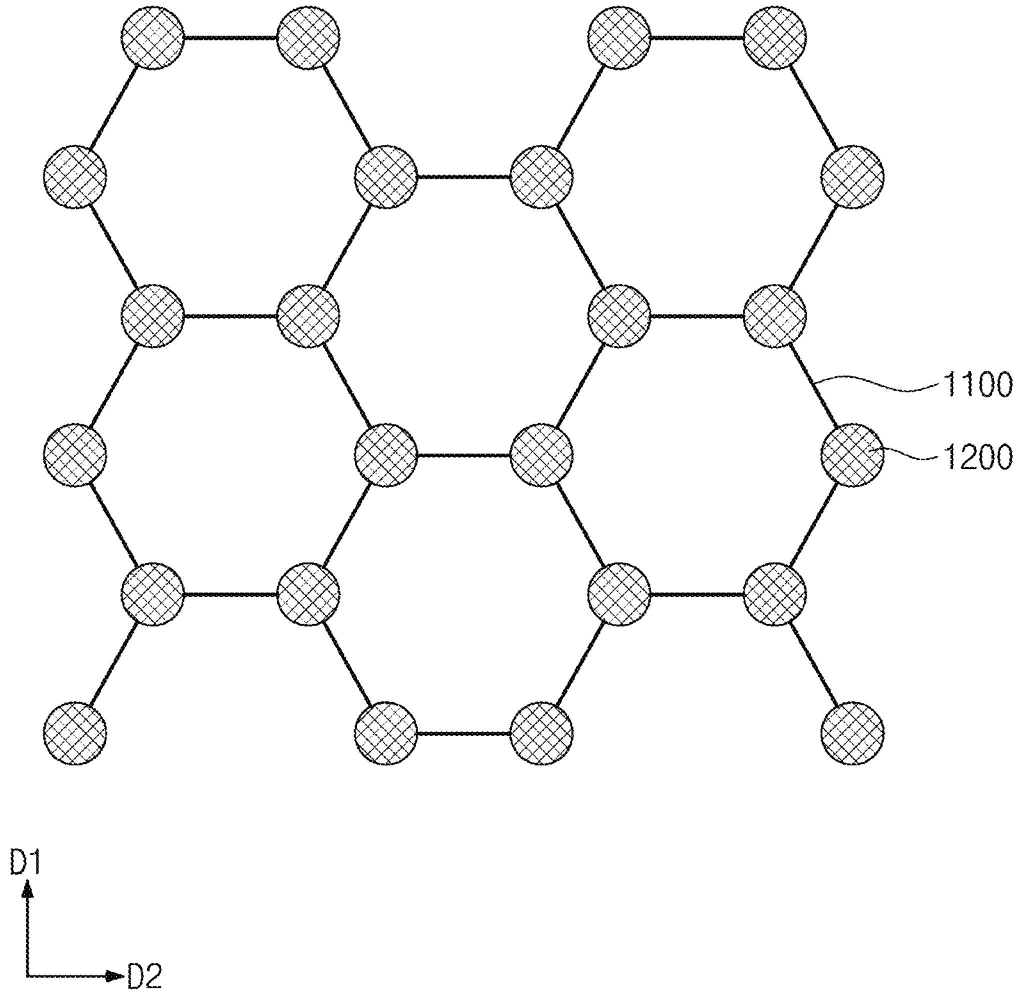
FIG. 7 is a plan view illustrating a mechanochromic array patch including a polymer connection part continuously connected in a hexagonal form.

FIGS. 6 and 7 are plan views illustrating various array design examples of a mechanochromic array patch. Referring to FIG. 6, the polymer connection part 1100 of the mechanochromic array patch may be continuously connected in a triangular form. Referring to FIG. 7, the polymer connection part 1100 may be continuously connected in a hexagonal form.

The mechanochromic array patch of the inventive concept may provide information about movement of a musculoskeletal system without distortion due to a patch size or an external power supply. Sensitivity and functionality of the patch may be improved by dividing a polymer connection part that is not stretchable and a color-changing part having stretchability and mechanochromic characteristics.

The mechanochromic array patch of the inventive concept is manufactured in a form of a skin-integrated patch attachable along skin flexure so that movement of a musculoskeletal system under skin may be detected in a locally concentrated form.

Although the embodiments of the present invention have been described, it is understood that the present invention should not be limited to these embodiments but various changes and modifications can be made by one ordinary skilled in the art within the spirit and scope of the present invention as hereinafter claimed.

What is claimed is:

1. A mechanochromic array patch comprising:

a plurality of separate stretchable mechanochromic color-changing parts, each being spaced apart from adjacent ones of the plurality, the plurality being arranged in a two-dimensional array form;

a plurality of polymer connection parts, each extending between and connecting adjacent ones of the plurality of separate stretchable mechanochromic color-changing parts; and a water-insoluble support part, wherein each of the plurality of polymer connection parts has a higher elastic modulus compared to each of the plurality of separate stretchable mechanochromic color-changing parts.

2. The mechanochromic array patch of claim 1, wherein each of the plurality of separate stretchable mechanochromic color-changing parts is configured to change in color according to a strain rate.

3. The mechanochromic array patch of claim 1, wherein each of the plurality of polymer connection parts includes a non-stretchable polymer.

4. The mechanochromic array patch of claim 1, wherein each of the plurality of separate stretchable mechanochromic color-changing parts includes a stretchable polymer and mechanochromic material.

5. The mechanochromic array patch of claim 4, wherein the stretchable polymer includes at least one of polydimethylsiloxane, poly-butylene adipate terephthalate (PBAT), or poly(styrene-block-butadiene styrene) (SBS).

6. The mechanochromic array patch of claim 4, wherein the mechanochromic material includes at least one of photonic crystal, piezophotonic materials, mechanophores-linked polymers, or microcrack structure.

7. The mechanochromic array patch of claim 1, wherein each of the plurality of polymer connection parts includes at least one of polyimide, photoresist, or resin.

8. The mechanochromic array patch of claim 1, wherein the water-insoluble support part includes at least one of polydimethylsiloxane, polystyrene, or poly(ethylene terephthalate) (PET).

9. The mechanochromic array patch of claim 1, wherein each of the plurality of separate stretchable mechanochromic color-changing parts further include a skin-adhesive material layer, wherein the material layer includes at least one of polyvinyl alcohol or hydrogel.

* * * * *